Figure 1:
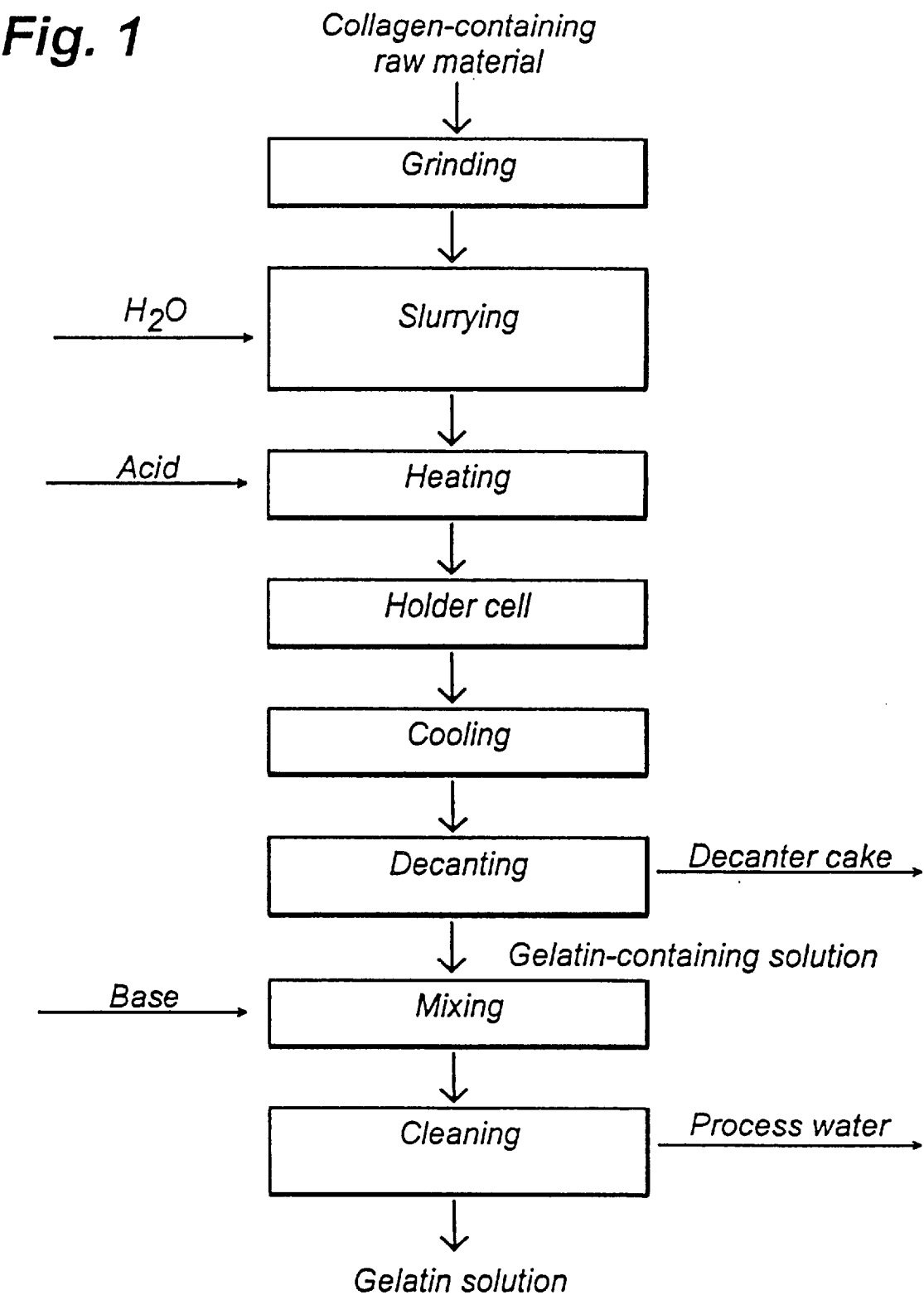

United States Patent [19]

Lilja et al.

[11] Patent Number: 5,877,287

[45] Date of Patent: Mar. 2, 1999

[54] METHOD FOR PRODUCING GELATIN

[75] Inventors: Mats Lilja, Södra Sandby; Mats Larsson, Lund, both of Sweden

[73] Assignee: Ellco Food AB, Sweden

[21] Appl. No.: 525,559

[22] PCT Filed: Jan. 31, 1994

[86] PCT No.: PCT/SE94/00071

§ 371 Date: Sep. 19, 1995

§ 102(e) Date: Sep. 19, 1995

[87] PCT Pub. No.: WO94/21739

PCT Pub. Date: Sep. 29, 1994

[30] Foreign Application Priority Data

Mar. 19, 1993 [SE] Sweden ................................ 9300912

[51] Int. Cl.⁶ .............................. C07K 1/00; C07K 14/00; C07K 17/00; A61K 38/17
[52] U.S. Cl. ........................ 530/355; 530/354; 530/350
[58] Field of Search ..................................... 530/355, 354, 530/350

[56] References Cited

U.S. PATENT DOCUMENTS 4,389,423  6/1983  Madsen .

FOREIGN PATENT DOCUMENTS

| | | |
|---|---|---|
| 0050431 | 4/1982 | European Pat. Off. . |
| 0 323 790 | 7/1989 | France . |
| 2747798 | 4/1979 | Germany . |
| 2207137 | 1/1989 | United Kingdom . |

OTHER PUBLICATIONS

Ward et al., Chapter 9, Raw Materials, The Science and Technology of Gelatin, pp. 295–364 : 1977.

Application of Enzymes in Gelatin Processing, Novo Enzymes : 1986.

Primary Examiner—Lynette F. Smith
Assistant Examiner—Brett Nelson
Attorney, Agent, or Firm—Cushman Darby & Cushman IP Group of Pillsbury Madison & Sutro LLP

[57] ABSTRACT

In a method for producing gelatin from collagen-containing raw material, the raw material is ground and mixed with water to form a slurry; the slurry is treated with an acid and heated in order to expose the collagen in the raw material; the pH and the temperature of the slurry are adjusted once more; the slurry is separated into a liquid portion and a solid residue; and the gelatin is recovered from the liquid portion.

15 Claims, 1 Drawing Sheet

METHOD FOR PRODUCING GELATIN

This invention relates to a method for producing gelatin from a collagen-containing raw material.

Gelatin is a natural product that is used primarily in the food industry, but also in the pharmaceutical, the photographic, the textile and the paper industry.

Gelatin is a protein obtained from collagen that occurs in the skin, connective tissue, bones and other parts of animals, mammals as well as fish. In the bone phase, the collagen is present in the form of a fibrous matrix surrounded by inorganic material. When looking at suitably-colored bone phase under the microscope, one sees that the bone phase is crisscrossed by densely-packed bundles of collagen fibres. Under an electron microscope, these fibres are seen to consist of fibrils that are about 400–1200 Å in diameter. The fibrils have a cross-striped structure similar to that of connective tissue. On average, collagen makes up almost a third of the bone phase, based on dry weight. The inorganic phase consists of small, densely-packed crystals (50×600 Å) having an X-ray diffraction pattern similar to that of hydroxyapatite, $3.Ca_3(PO_4)_2.Ca(OH)_2$.

The collagen fibrils are composed of rod-shaped collagen molecules (tropocollagen) having a length of 300 nm and a thickness of 1.5 nm. The tropocollagen is composed of three polypeptide chains, so-called $\alpha$-chains, forming a triple helix. In the fibrils, the tropocollagen is cross-linked by covalent bonds primarily located at the molecule ends, the so-called telopeptides. Native tropocollagen is highly resistant to alkaline, acid and enzymatic hydrolysis, owing to its densely-packed helix structure. However, the telopeptides do not have such a high resistance, since they are not integrated in the helix structure, but may be regarded as randomised or globular regions.

When the collagen molecule is heat-denatured, the triple helix is untwined, and free polypeptide chains are formed, i.e. gelatin is obtained. When the collagen molecules are present in such tissue as bone tissue, the situation is more complex. In order that the tropocollagen molecules should be dissolved and heat-denatured to gelatin, the covalent cross-links between the molecules have to be broken up. This can be brought about e.g. by high-temperature heating (autoclaving). However, such heating not only breaks up the cross-links, but also causes random hydrolysis of the bonds in the tropocollagen, resulting in gelatin of poor quality. In the method most commonly used, the telopeptides and, hence, the cross-links are hydrolysed at a low temperature (15°–25° C.), leaving the triple helix intact and rendering the tropocollagen extractible.

In conventional techniques for producing gelatin from bone, the whole bones or bones divided into pieces are first demineralized completely with acid at a low temperature and for several days, so that the collagen matrix is exposed and ossein is obtained. Demineralization, which is performed in a separate step, implies treatment at a pH<2, in which large amounts of acid are consumed. Separate and complete demineralization is an extremely important part of today's gelatin production on the basis of bone raw material. The purpose of such demineralization is to dissolve the calcium salts in the bone, thereby to expose the collagen matrix. Calcium is present in the form of hydroxyapatite, which is dissolved by treatment with diluted hydrochloric acid. After demineralization, the ossein is "conditioned" by means of alkali, such as lime or lime milk, for 1–6 months at a low temperature. In this treatment, the intramolecular bonds are broken up, the solution is neutralised and the collagen is extracted at an elevated temperature (50°–95° C.). The collagen is denatured, and gelatin is obtained.

Present-day methods for producing gelatin distinguish between whether the raw material employed is bone or hide (split, rind) and other connective-tissue material.

Containing no minerals, hide and connective tissue are not subjected to any demineralization, but are otherwise treated in the same way as bone raw material.

Alternatively, "conditioning" may imply acid treatment, which means that, after being washed and optionally divided into smaller pieces, the raw material is left in an acid bath for 1–4 days at a low temperature. Also the acid conditioning takes place at a pH<2. The type of pretreatment employed chiefly depends on the origin of the raw material. Ossein, calf and cattle hides are primarily treated according to the alkaline method, whereas bacon rind is especially suited for the acid method owing to its high fat content. Furthermore, old hides require treatment according to the alkaline method, on account of the many cross-links found in such material. In the case of younger hides, the acid method may well be used.

The alkaline treatment, in which ossein and/or hide material are treated for a long time (up to 6 months) with lime or lime milk (pH about 11–12), requires extremely large amounts of process water and chemicals, since the water has to be changed several times. Thus, up to 1000 l of water may be needed to produce 1 kg of gelatin. Moreover, the treatment with lime is followed by deliming, which also is a complex method step.

Although the acid treatment is not as time-consuming as the alkaline treatment, one or a few days are nevertheless needed to expose most of the collagen.

Furthermore, conventional techniques require a great number of extraction steps (up to 6 or 7) to yield an acceptable result. The quality of the gelatin obtained is not homogeneous, but generally deteriorates with the number of extraction steps. High-quality gelatin is obtained in the first steps only.

Thus, the drawbacks of conventional methods chiefly reside in the extremely long treatment times and the considerable amounts of process water and chemicals required, resulting in large amounts of waste and associated environmental problems. A further drawback is that different raw materials require different treatments. Naturally, the long treatment times have an adverse effect on the quality and the yield of gelatin.

German Patent Specification 27 47 798 discloses a method for extracting collagen from sinews and hides and then processing the collagen to produce gelatin. In this method, alkaline treatments alternate with different washing stages for recovering collagen from the raw material employed. Considerable amounts of process water are supplied and drawn off during implementation of the method, resulting in large amounts of waste and associated environmental problems, as indicated in the foregoing. Furthermore, the German method can only be applied to sinews and hides.

EP-B1-0 323 790 describes a method for producing gelatin from bone meal. Like other prior-art methods, this method includes different washing steps which, however, alternate with acid treatments. Thus, also this method yields large amounts of process water with ensuing environmental problems.

Depending on the field of application, different quality requirements are placed on the gelatin. Gelling capacity and gel strength are two important properties of gelatin. Conventionally, gel strength is indicated in Bloom numbers. Thus, a Bloom number of >about 240 indicates high-quality gelatin, a Bloom number of about 120–240 indicates average-quality gelatin, and a Bloom number of <about 120 indicates low-quality gelatin.

Accordingly, it is a desideratum to provide cost-effective and environmentally-friendly production of high-quality gelatin, which would involve shorter residence times, less process water and chemicals and, hence, less waste.

One object of the invention is to provide a cost-effective and environmentally-friendly method for producing high-quality gelatin.

Another object of the invention is to provide a method for producing gelatin, which can be used for different sorts of collagen-containing raw material as well as mixtures of such materials.

According to the invention, these objects are achieved by a method for producing gelatin from a collagen-containing raw material, comprising the steps of a) grinding the raw material to a particle size not exceeding 1 mm, b) mixing the ground raw material with water to form a slurry, c) subjecting the slurry from step b), in optional order, to an adjustment of the pH to 2–5 and to an adjustment of the temperature to 60°–130° C. for a time of from 1 s to 1 h, d) adjusting the temperature of the slurry once more, e) separating the slurry into a gelatin-containing liquid portion and a solid residue, f) adjusting the pH of the slurry or the liquid portion before or after, respectively, the separation, and g) recovering the gelatin from the liquid portion in filtration steps and/or other cleaning steps, with essentially no removal of process water in steps a)–f).

The inventive method can be applied to different collagen-containing materials, such as hides, split, rind, gristle, sinews, intestines, stomachs, connective-tissue material and different types of bone material from animals.

The inventive method may also include a partial demineralization treatment and/or an enzyme treatment in order to improve the yield even further. If so, such treatments are carried out prior to step c). However, a good yield is obtained also without any such additional treatments. Optionally, the raw material employed can be defatted prior to grinding.

If an enzyme treatment involving pH and temperature adjustments is to be carried out prior to step c), the pH of the slurry of ground raw material should first be adjusted to the proper pH of the enzyme employed, thus preventing denaturation of the enzyme due to an improper pH.

The inventive method for producing gelatin can be implemented in continuous or semicontinuous fashion as well as batchwise.

The method according to the invention is schematically illustrated in FIG. 1. Any collagen-containing raw material may be used. To begin with, the raw material is ground to a suitable particle size. Then, the particles are slurried, and the resulting slurry is acidified by the addition of an acid and is heated, the elevated temperature being maintained for a certain period of time. Thereafter, the treated slurry is cooled, and solid material is separated from the gelatin-containing liquid portion. In order to increase the pH, a base is added to the liquid portion under agitation, and the gelatin-containing solution is then processed and cleaned according to prior-art techniques, so as to form a gelatin solution. It is only at this stage that process water is separated from the production.

The base added in order to raise the pH after the acid treatment may further be added before the separation of solid material instead of after.

The method according to the invention will now be described in more detail.

The raw material employed is obtained e.g. from slaughterhouses, meat-cutting centres or the fish industry. By "collagen-containing raw material" is here meant unmixed as well as mixed collagen-containing raw material. The raw material employed may be one or a few of the materials mentioned above, originating from all types of mammals as well as fish.

The collagen-containing raw material is ground to an average particle size not exceeding 1 mm. The grinding, either wet grinding or dry grinding, is performed in one or more steps with the aid of suitable, conventional equipment. The average particle size should be about 1 mm at the most, preferably about 300 $\mu$m at the most. An average particle size of<100 $\mu$m is especially suitable, and an average particle size of<40 $\mu$m is most preferred. Optionally, the material may be defatted prior to grinding, e.g. to a fat content not exceeding 3% by weight. Although such a step is not critical, a low fat content facilitates subsequent process steps.

The ground material is mixed with water to form a slurry, and the pH and the temperature are then adjusted in optional order. The pH is suitably adjusted to 2–5, preferably 3.5–5. The temperature suitably is 60°–130° C., preferably 80°–110° C. The slurry is kept at this temperature for a period of time in the range of from 1 s to 1 h, preferably in the range of 5–40 min, and most preferred in the range of 10–30 min. The pH, the temperature and the time are determined according to the degree of grinding and the quality requirements placed on the gelatin to be produced.

The amount of collagen converted to gelatin increases proportionately to the reduction of particle size, the decrease in pH, the increase in temperature and the prolongation of the residence time. However, the more extensive the treatment to which the material is subjected, the lower the quality of the resulting gelatin. Thus, these parameters have to be so combined that the aimed-at gelatin quality is obtained. In some applications, lower-quality gelatin may, of course, do.

After grinding, the material may optionally be subjected to a brief and partial demineralization and/or an enzyme treatment in order to enhance production efficiency and increase the total yield of gelatin. The partial demineralization is performed with an acid, such as phosphoric acid. The enzyme treatment may be performed with one or more enzymes, or a mixture of enzymes. Different proteolytic enzymes have different specificities for different amino acid sequences, as well as different pH- and temperature-dependence. Examples of suitable enzymes are alkaline, bacterial proteases. In the enzyme treatment, the pH of the slurry is adjusted to a suitable pH in view of the enzyme employed. A specific example of an enzyme that may be used is ESPERASE® (Novo, Denmark), which requires a pH of about 7. Conveniently, no more than a per cent or so of the enzyme is added, e.g. 0.5%. The enzyme in the slurry is allowed to act a few hours at room temperature, and the collagen is then extracted from the slurry at an elevated temperature, as above.

The pH is adjusted by means of an acid, such as hydrochloric acid, phosphoric acid, sulphuric acid, nitric acid or acetic acid. It is not of decisive importance which acid is used in the inventive method, but basically all acids may be employed, including organic as well as inorganic acids and mixtures thereof. Some acids are, however, more effective than others. It may be advantageous to use phosphoric acid in order to decrease the pH and to use calcium dihydroxide in order to increase the pH, since these two acids form a type of calcium phosphate that is a natural ingredient of bone material. It is less expensive to use hydrochloric acid and sodium hydroxide, but the final gelatin solution obtained after the separation will then have a higher salt content.

As to the temperature adjustment at this stage of the inventive method, the reaction rate increases with the temperature. There is basically no maximum temperature, but the organic material is rapidly decomposed at very high temperatures. The residence time required will then be extremely short and difficult to regulate at such high temperatures.

If low-quality gelatin, such as bone glue, is an acceptable or aimed-at product, the temperature may, of course, be increased in order to reduce the residence time.

The residence time is achievable in a conduit system through which the slurry is pumped or in a tank where the slurry is kept for a certain period of time. However, this last embodiment implies that different parts of the slurry will have different residence times, and this embodiment therefore should not be used in the case of extremely short residence times.

After this treatment, the temperature is adjusted in order to complete the reaction. Conveniently, the temperature is adjusted to 100° C. at the most, for instance to 60° C.

After this temperature adjustment, the slurry is separated into a liquid portion and a solid residue. The liquid portion contains the gelatin recovered from the collagen. Depending on the raw material employed, the solid residue contains undissolved bone, salts, insoluble proteins, and so forth. Preferably, the solid residue is washed in order to recover as much gelatin as possible. The separation can be carried out in a conventional decanter, but other conventional equipment may of course be used.

The pH should also be adjusted when the need arises. This can be done either before or after the separation of the slurry into a liquid portion and a solid residue. The pH suitably is 5.5–6.0, for instance 5.5. Various alkaline chemicals may be used for adjusting the pH at this stage. As mentioned in the foregoing, calcium hydroxide is advantageously used, and it is generally an advantage to use an alkaline chemical reacting with the acid to form an insoluble substance. As a result, the gelatin solution produced will have a lower salt content than it would have had if the chemicals had not reacted with one another. The temperature and pH adjustments performed in this step are designed to strike a balance between decomposition and microbiological activity. Since gelatin gels at about 30° C., it is vital that the temperature be maintained well above this temperature for the remainder of the process.

The resulting gelatin solution may be used as such, with the yield and the quality obtained, but the solution may also undergo additional treatment and cleaning steps. If the solids are remixed with water and homogenised and then subjected to yet another pH adjustment to a pH of 2–5 as well as a temperature adjustment to 60°–130° C. for a period of time ranging from 1 s to 1 h, to be followed by cooling, etc., the yield can be increased even further. Naturally, this process can be repeated any number of times. The solid residues from these steps are dried separately.

The gelatin-containing liquid portion may then be further treated in order to recover dry gelatin. Depending on the aimed-at gelatin quality, the gelatin solution undergoes different filtration steps and/or other cleaning steps. Also, the different filtration and cleaning steps depend on the raw material employed. A few examples of filtration and cleaning steps are given below.

The solutions obtained from the different decanting steps are mixed and filtered, e.g. by two different filters, in order to remove particles and coarse material. For instance, 50-$\mu$m and 25-$\mu$m filters may suitably be used. In order to produce high-quality gelatin, it is necessary to remove salts and peptides, which is best done by ultrafiltration, which also concentrates the solution. Generally, ultrafiltration does not remove all the salts, but ion exchange may be needed to achieve a sufficiently low salt content. After these steps, the solution may still be cloudy and have a certain taste. If the solution contains fat, this can be removed with the aid of special fat-absorbing filters. Color can be removed by active-carbon filtration, and final clarity can be obtained by filtration through a fine filter.

Being of conventional design, the equipment used in the different steps of the inventive method will not be described in more detail here. Also, the choice of appropriate equipment is a measure of convenience obvious to those skilled in the art.

The present inventions yields high-quality gelatin, generally having a Bloom number above 250, while involving low costs, short process-times and small process volumes, as compared with the prior-art methods mentioned in the foregoing. Thus, the inventive method for producing gelatin is cost-effective as well as environmentally-friendly. Compared with the above prior-art methods for producing gelatin from bone raw material, the inventive method is especially advantageous in dispensing with the separate step of complete demineralization as well as the long residence time of alkaline conditioning. Furthermore, no or practically no process water is drawn off from the process until the slurry has been separated into a gelatin-containing liquid portion and a solid residue and the pH has been adjusted. In the method according to the invention, the collagen molecules are exposed in different fashion.

The method according to the invention may be implemented in one step, i.e. continuously, which is unfeasible with prior-art methods owing to the long residence times. Moreover, the gelatin solution obtained after the separation step in the inventive method is fully acceptable as regards yield as well as quality. Most prior-art methods, on the other hand, require up to 6 or 7 extraction steps to give the same yield. The invention also has the considerable advantage of enabling use of one and the same method, regardless of the origin of the raw material employed, as well as the use of unmixed or mixed raw material.

Another considerable advantage associated with the invention is that the amount of waste leaving the process in the form of process water is insignificant, compared with prior-art methods. Naturally, this automatically enhances cost effectiveness.

The invention will now be illustrated in more detail with the aid of a few non-restricting Examples.

EXAMPLE 1

This Example involves a continuous method. Bone of food quality obtained from slaughterhouses was defatted in an Alfa Laval Centribone process and wet-ground to an average particle size of 80 $\mu$m, water being added in such an amount that a slurry having a dry solids content of 20% by weight was obtained. The pH of the slurry was adjusted to 3.5-by means of phosphoric acid. Then, the slurry was heated to 110° C. in an ALFA LAVAL-CONTHERM® scraped-surface heat exchanger, and the slurry was kept at this temperature for 15 min in a conduit system. After 15 min, the pH was adjusted to 5.5 by means of calcium dihydroxide.

Thereafter, the temperature was adjusted to 60° C. in ALFA LAVAL-CONTHERM®. The slurry was then transferred to an Alfa Laval decanter NX409, where the solids were separated from the water. The solids were mixed with fresh water at a temperature of about 60° C. to a homogeneous slurry, which was transferred to another decanter. The liquid portion obtained in this treatment was mixed with the liquid portion obtained in the first treatment. About 75% of the collagen had been converted to gelatin in this treatment. By using two decanters, about 80% of the gelatin was recovered to the liquid portion. The resulting solution, which consisted of the mixed liquid portions, was filtered in order to remove particles and other coarse material. The solution was filtered first through a 50-μm filter and then through a 25-μm filter.

Thereafter, the solution was treated in an ultrafiltration apparatus HSK131 from Alfa Laval, having membranes from Koch with a cut-off of 5000u. In this apparatus, the solution was concentrated, and salts and peptides were removed. After ultrafiltration, the solution now having a dry solids content of 20% was subjected to an ion-exchange treatment in order to remove most of the remaining salts. Then, the solution was filtered in three steps.

In the first step, the solution was filtered in order to remove any remaining fat. In the second step, the solution was filtered through active carbon in order to remove colour and improve the taste and smell. In the third step, the solution was filtered through a polishing filter in order to achieve final clarity. Thereafter, the solution was cooled so that the gelatin gelled, and so-called noodles then formed in a scraped-surface heat exchanger, e.g., ALFA LAVAL-CONTHERM®, and drying was carried out. The resulting gelatin had a Bloom number of 290, a viscosity of 42.3 mPs, and a clarity of 21 NTU, as measured by means of a Hach Ratio Turbidimeter. NTU, which is a measure of clarity, stands for Nephelometric Turbidity Units. The isoelectric point IEP was 7.3.

EXAMPLE 2

Bone of food quality obtained from slaughterhouses was defatted in an Alfa Laval Centribone process. By means of a hydrocyclone, the bone material was separated into two fractions, one containing most of the bone and one chiefly composed of softer material. The bone fraction was used in this Example.

The bone was mixed with water to a slurry having a dry solids content of about 20% and was ground to a particle size of about 1–2 mm in a Simo industrial mill. The slurry was then transferred to a Dorr-Oliver Supraton mill equipped with conical grinding gear. After this treatment, the average particle size was about 200 μm. The slurry was further treated in a Sussmeyer pearl mill to a final average particle size of about 20 μm. The pH of the slurry was adjusted to 4 by means of phosphoric acid, and the temperature was adjusted to 100° C. in an ALFA LAVAL-CONTHERM®. The residence time was 5 min. The pH was then adjusted to 5.5 by means of calcium dihydroxide, and the temperature was adjusted to 60° C. Thereafter, the treatment proceeded as in Example 1 above.

In this Example, 85% of the collagen was converted to gelatin having a Bloom number of 310 and a viscosity of 46.3 mPs.

EXAMPLE 3

In this Example, the inventive method was tested on a laboratory scale. The tests were carried out with and without an enzyme treatment, and with and without ultrafiltration of the gelatin solution. * indicates additional steps of enzymatic treatment.

1) 2 kg of bone meal (particle size of 40–125 μm) was mixed with 6 kg of ice water to a slurry.
2) The bone meal was partially demineralised by means of concentrated phosphoric acid to a pH of 3.
3) * The pH was adjusted to about 7.
4) * ESPERASE® was added (0.5%), and the slurry was agitated over night.
5) The pH was adjusted to 3.5.
6) Extraction was performed by batchwise (2 l) heating to 90° C. in a microwave oven (about 15 min).
7) The solution was neutralised by means of $Ca(OH)_2$, and was centrifuged and filtered on cellulose with the aid of filter equipment.
8) Part of the solution was dried at once, and part of the solution was subjected to ultrafiltration.
9) The yield, the Bloom number, the viscosity, the clarity and the ash content were determined.

The results of these tests are accounted for in the Table below.

TABLE

The results of tests with and without enzyme treatment, as well as with and without ultrafiltration (UF), of the gelatin produced.

| Test | Bloom number | Viscosity (mPs) | Clarity (NTU) | Ash content (%) | Yield* (%) |
| --- | --- | --- | --- | --- | --- |
| Without enzyme | 302** | — | — | 18.8 | |
| Without enzyme + UF | 300 | 37 | 150 | 3.9 | 73 |
| Enzyme | 182 | 29 | — | 12.2 | |
| Enzyme + UF | 256 | 35 | 249 | 6.8 | 87 |

*Total yield after 2 extraction stages.
**Bloom number measured on half the amount.

What is claimed is:

1. A method for producing gelatin from a collagen-containing raw material without a requirement for a demineralization step, said method consisting essentially of the steps of
   a) grinding the raw material to a particle size not exceeding 1 mm,
   b) mixing the ground material with water to form a slurry,
   c) adjusting the pH of the slurry to 2–5 and adjusting the temperature of the slurry to 60°–130° C. for a time between 1 second and one hour,
   d) adjusting the temperature of the slurry to 100° C. or below,
   e) separating the slurry into a gelatin-containing liquid portion and a solid residue,
   f) increasing the pH of the slurry or the liquid portion before or after the separation of step e), and
   g) recovering the gelatin from the liquid portion,
   wherein steps a) to f) are performed with essentially no removal of process water.

2. The method as set forth in claim 1, wherein the raw material is wet-ground or dry-ground.

3. A method as set forth in claim 1, which is implemented in continuous or semicontinuous fashion or batchwise.

4. The method as set forth in claim 1, wherein the raw material is ground to a particle size of <about 300 μm.

5. The method of claim 4 wherein the particle size is <100 μm.

6. The method of claim 5 wherein the particle size is <40 μm.

7. The method as set forth in claim 1, wherein the slurry in step c) is treated with an acid to attain a pH of 3.5–5.

8. The method as set forth in claim 7, wherein the acid is selected from the group consisting of HCl, $H_3PO_4$, $HNO_3$, $CH_3COOH$ and $H_2SO_4$, and mixtures thereof.

9. The method as set forth in claim 1, wherein the slurry in step c) is heated to a temperature of about 80°–110° C.

10. The method as set forth in claim 1, wherein the treatment time in step c) is 5–40 min.

11. The method as set forth in claim 1, wherein the raw material is defatted prior to grinding.

12. The method as set forth in claim 1, wherein the gelatin from the liquid portion is recovered by filtering in one or more steps.

13. The method of claim 1 wherein pH is adjusted prior to temperature in step c).

14. The method of claim 1 wherein temperature is adjusted prior to pH in step c).

15. A method as set forth in any one of claims 2–7, 9–10, or 11-6 or 1–14, wherein the treatment time in step c) is 10–30 minutes.

\* \* \* \* \*